(12) United States Patent
Pjetri et al.

(10) Patent No.: US 11,982,665 B2
(45) Date of Patent: May 14, 2024

(54) OIL QUALITY SENSOR

(71) Applicant: Dodge Industrial, Inc., Oxford, CT (US)

(72) Inventors: Erald Pjetri, Cracow (PL); Stefan Pypec, Cracow (PL); Artur Rdzanek, Simpsonville, SC (US); Brandon LeRoy, Anderson, SC (US); Greg Hewitt, Taylors, SC (US); Isaac O'Brien-Herr, Greer, SC (US)

(73) Assignee: Dodge Industrial, Inc., Oxford, CT (US)

( * ) Notice: Subject to any disclaimer, the term of this patent is extended or adjusted under 35 U.S.C. 154(b) by 219 days.

(21) Appl. No.: 16/953,893

(22) Filed: Nov. 20, 2020

(65) Prior Publication Data

US 2022/0163505 A1 May 26, 2022

(51) Int. Cl.
*G01N 33/28* (2006.01)
*G01N 21/01* (2006.01)
*G01N 27/22* (2006.01)

(52) U.S. Cl.
CPC .......... *G01N 33/2888* (2013.01); *G01N 21/01* (2013.01); *G01N 27/221* (2013.01); *G01N 33/2805* (2013.01)

(58) Field of Classification Search
CPC .. G01N 33/2888; G01N 21/01; G01N 27/221; G01N 33/2805
See application file for complete search history.

(56) References Cited

U.S. PATENT DOCUMENTS

| | | | | |
|---|---|---|---|---|
| 3,497,034 A | * | 2/1970 | Eddy, Jr. | ................. G01N 9/36 73/19.01 |
| 4,109,997 A | * | 8/1978 | Iverson | ................ G02B 27/642 385/26 |
| 4,926,120 A | | 5/1990 | Veronesi et al. | |
| 5,357,197 A | | 10/1994 | Sorkin | |
| 5,402,113 A | | 3/1995 | Naas | |

(Continued)

FOREIGN PATENT DOCUMENTS

| | | |
|---|---|---|
| CN | 101435788 B | 5/2012 |
| CN | 202305460 U | 7/2012 |

(Continued)

OTHER PUBLICATIONS

Fendri, Ahmed, et al., "Dielectric Spectroscopy for Assessment of Water Content in Edible Oils", 14th International Multi-Conference on Systems, Signals & Devices (SSD), 2017 (5 pp).

(Continued)

*Primary Examiner* — Alexander Satanovsky
*Assistant Examiner* — Sharah Zaab
(74) *Attorney, Agent, or Firm* — Ruggiero McAllister & McMahon LLC

(57) ABSTRACT

A sensor for monitoring the quality of oil in mechanical machinery is provided. The sensor includes a portion that is sealed from the oil which contains electric circuitry to process signals received from the sensing elements. Another portion of the sensor is exposed to the oil and contains one or more sensing elements to sense one or more properties of the oil. The sensed properties may include electrical properties, temperature properties and/or optical properties.

28 Claims, 8 Drawing Sheets

(56) References Cited

U.S. PATENT DOCUMENTS

| | | | |
|---|---|---|---|
| 5,459,406 A | | 10/1995 | Louge |
| 5,789,665 A | * | 8/1998 | Voelker ............... G01N 33/2888 |
| | | | 422/82.01 |
| 5,824,889 A | * | 10/1998 | Park .................... G01N 33/2888 |
| | | | 701/29.5 |
| 5,852,404 A | | 12/1998 | Amini |
| 6,717,667 B2 | | 4/2004 | Abraham et al. |
| 6,718,819 B2 | | 4/2004 | Schoess |
| 6,937,332 B2 | | 8/2005 | Engler et al. |
| 7,204,128 B1 | | 4/2007 | Liu et al. |
| 7,383,731 B2 | | 6/2008 | Liu et al. |
| 9,927,415 B2 | | 3/2018 | Baumann et al. |
| 9,970,903 B1 | * | 5/2018 | Gerardi ................ G01N 29/032 |
| 2003/0179919 A1 | * | 9/2003 | Goldberg ........... G01N 21/9501 |
| | | | 382/141 |
| 2004/0267465 A1 | | 12/2004 | Sanchez Pina et al. |
| 2005/0066711 A1 | | 3/2005 | Discenzo |
| 2006/0150727 A1 | * | 7/2006 | Estes ....................... E21B 47/09 |
| | | | 73/152.56 |
| 2008/0024761 A1 | | 1/2008 | Kong et al. |
| 2008/0289400 A1 | * | 11/2008 | Quist ...................... G01N 11/16 |
| | | | 73/1.02 |
| 2010/0109686 A1 | | 5/2010 | Zhe et al. |
| 2012/0013354 A1 | * | 1/2012 | Bowler ................. G01N 27/226 |
| | | | 324/686 |
| 2014/0123731 A1 | | 5/2014 | Basu |
| 2014/0266065 A1 | | 9/2014 | Von Herzen et al. |
| 2015/0323369 A1 | | 11/2015 | Marquardt |
| 2016/0084774 A1 | | 3/2016 | Shirata |
| 2016/0313237 A1 | * | 10/2016 | Young ................. G01N 21/3577 |
| 2017/0363529 A1 | | 12/2017 | Ture et al. |
| 2018/0023414 A1 | | 1/2018 | Hagen et al. |
| 2018/0045501 A1 | * | 2/2018 | Elmaanaoui ....... G01B 9/02091 |
| 2018/0107203 A1 | | 4/2018 | Hagen et al. |

FOREIGN PATENT DOCUMENTS

| | | | | |
|---|---|---|---|---|
| CN | 202947988 U | | 5/2013 | |
| CN | 204044101 U | | 12/2014 | |
| CN | 104165908 B | | 2/2017 | |
| CN | 106376168 | * | 2/2017 | ............ H01L 21/67 |
| CN | 105181534 B | | 2/2018 | |
| CN | 108007980 A | | 5/2018 | |
| DE | 10100773 A1 | | 7/2002 | |
| DE | 10131106 A1 | | 1/2003 | |
| DE | 10225716 A1 | | 1/2004 | |
| EP | 0159094 B1 | | 10/1985 | |
| EP | 0223400 A2 | | 5/1987 | |
| EP | 1462775 | * | 9/2004 | ............ G01F 23/26 |
| EP | 3276347 A1 | | 1/2018 | |
| FR | 2242682 A1 | | 3/1975 | |
| GB | 2284891 B | | 6/1995 | |
| JP | 9-318574 A | | 12/1997 | |
| KR | 10-0638121 B1 | | 10/2006 | |
| RU | 2192001 C1 | | 10/2002 | |
| RU | 2209422 C1 | | 7/2003 | |
| RU | 2397482 C1 | | 8/2010 | |
| WO | 2007044308 A1 | | 4/2007 | |
| WO | 2011022254 A2 | | 2/2011 | |
| WO | 2011065340 A1 | | 6/2011 | |

OTHER PUBLICATIONS

Haiden, Christph, et al., "A Microfluidic Chip and Dark-Field Imaging System for Size Measurement of Metal Wear Particles in Oil", IEEE Sensors Journal, vol. 16, No. 5, Mar. 1, 2016 (8 pp).

Coronado, D., et al., "Assessment and validation of oil sensor systems for on-line oil condition monitoring of wind turbine gearboxes", 2nd International Conference on System-Integrated Intelligence: Challenges for Product and Production Engineering, Procedia Technology 15 2014, 2017 (8 pp).

Ortiz, David, et al., "Combined Lubrication Monitor for On-Line Gearbox Health Assessment", 2011 (8 pp).

Ding, Yongbin, et al., "An online debris sensor system with vibration resistance for lubrication analysis", Review of Scientific Instruments, 2016 (10 pp).

Hongbo, Fan, et al., "Design and Noise Control of the Portable Wear Debris Concentration Detector", International Conference on Measuring Technology and Mechatronics Automation, 2009 (4 pp).

Harkemanne, Etienne, et al., "Analysis and Testing of Debris Monitoring Sensors for Aircraft Lubrication Systems", MDPI Proceedings, www./mdpi.com/journal/proceeds, Jul. 15, 2018 (7 pp).

Metwally, Ibrahim A., et al., "Behaviour of electrical double layer under oil flow and voltage application inside a capacitive sensor", www.ietdl.org, Published in IET Science, Measurement & Technology, 2015 (9 pp).

Edmonds, Jack, et al., "Detection of Precursor Wear Debris in Lubrication Systems", Innovative Dynamics, Inc., 2000 (5 pp).

Cho, Jaedong, et al., "Capacitive sensor for automotive engine oil degradation using wireless network", School of Electrical Engineering and Computer Science, 2010 International Symposium on Advanced Packaging Materials: Microtech, 2010 (4 pp).

Wu, Kuo-Ting, et al., "Engine Oil Condition Monitoring Using High Temperature Integrated Ultrasonic Transducers", International Journal of Prognostics and Health Management, 2011 (7 pp).

Du, L., et al., "A microfluidic Inductive Pulse Sensor for Real Time Detection of Machine Wear", MEMS 2011, Cancun, Mexico, 2011 (4 pp).

Sun, Liquan, et al., "Analysis of Performance and Capcitance Sensitivity Distributions of Sensor for Electrical Capacitance Tomography System", Proceedings of the 6th World Congress on Intelligent Control and Automation, 2006 (5 pp).

Assaad, Maher, et al., "An Interface Circuit Design Based on Differential Capacitive Sensors for Accurate Measurement of Water Contents in Crude Oil", Electrical and Electronics Engineering Department, 2012 (4 pp).

Tayyab, Muhammad, et al., "A Radio Frequency Sensor Array for Dielectric Constant Estimation of Multiphase Oil Flow in Pipelines", IEEE Sensors Journal, vol. 17, No. 18, 2017 (8 pp).

Aslam, Muhammad Subair, et al., "Differential Capacitive Sensor Based Interface Circuit Design for Accurate Measurement of Water Content in Crude Oil", Dept. Electrical and Electronics engineering, 2014 (6 pp).

Dempsey, Paula J., et al., "Decision Fusion Analysis Detects Spiral Bevel Gear Damage", IEEE AES Systems Magazine, 2003 (7 pp).

Ren, Qing-Ying, et al., "A New Method for Real-Time Measuring the Temperature-Dependent Dielectric Constant of the Silicone Oil", IEEE Sensors Journal, vol. 16, No. 24, 2016 (6 pp).

Wang, Qiufang, et al., "Failure Diagnosis Technology Discussion of Vehicle Based on Oil Detection", 2015 Prognostics and System Health Management Conference-Beijing, 2015 (5 pp).

Lee, Rae Duk, et al., "A coil-Type Capacitive Sensor for Measurement of the Deterioration of Engine Oil", Korea Research Institute of Standards and Science (KRISS), 2002 (2 pp).

Liu, Ruochen, et al., "A Review on Electrostatic Monitoring", 2017 International Conference on Sensing, Diagnostic, Prognostics, and Control, 2017 (4 pp).

Bozchalooi, I. Soltani, et al., "Enhancement of the Signals Collected by Oil Debris Sensors", 2008 American Control Conference, 2008 (6 pp).

Feng, Song, et al., "An Inductive Debris Sensro Based on a High-Gradient Magnetic Field", IEEE Sensors Journal, vol. 19, No. 8, 2018 (8 pp).

Kim, Sunghyun, et al., "Degradation level monitoring sensor for insulating oil of power transformer using capacitive high aspect ratio of electrodes", The 13th International Conference on Solid-State Sensors, Actuators and Microsystems, Seoul, Korea, 2005 (4 pp).

Hongxiang, Tian, et al., "Application of Neural Network to Diesel Engine SOA", 2011 Third International Conference on Measuring Technology and Mechatronics Automation, 2011 (4 pp).

Jian, Wang, et al., "Application of relevance vector machine in the engine oil wear particle fault diagnosis", 2013 2nd International Symposium on Instrumentation and Measurement, Sensor Network and Automation (IMSNA), 2013 (4 pp).

(56) References Cited

OTHER PUBLICATIONS

Nan, Xie, et al., "Development of Online Measuring Instrument for Water-in-oil percentage based on MCU", 2009 International Forum on Information Technology and Applications, 2009 (3 pp).

He, Yaming, et al., "Analysis of Reverse-double-excitation Solenoid Wearing Debris Sensor", School of Automation Science and Electrical Engineering, 2017 (4 pp).

Ding, Yongbin, et al., "A Design of oil debris monitoring and sensing system", Guilin University of Electric Technology, 2015 (6 pp).

Xupeng, Zhao, et al., "Experimental study on the influence of coil diameter on double coil multi-parameter impedance detection sensor", 2017 IEEE 13th International Conference on Electronic Measurement & Instruments, 2017 (6 pp).

Han, Zhibin, et al., "Characteristics Study of In-situ Capacitive Sensor for Monitoring Lubrication Oil Debris", MDPI Sensors 2017, 17, 2851, www.mdpi.com/journal/sensors, 2017 (13 pp).

* cited by examiner

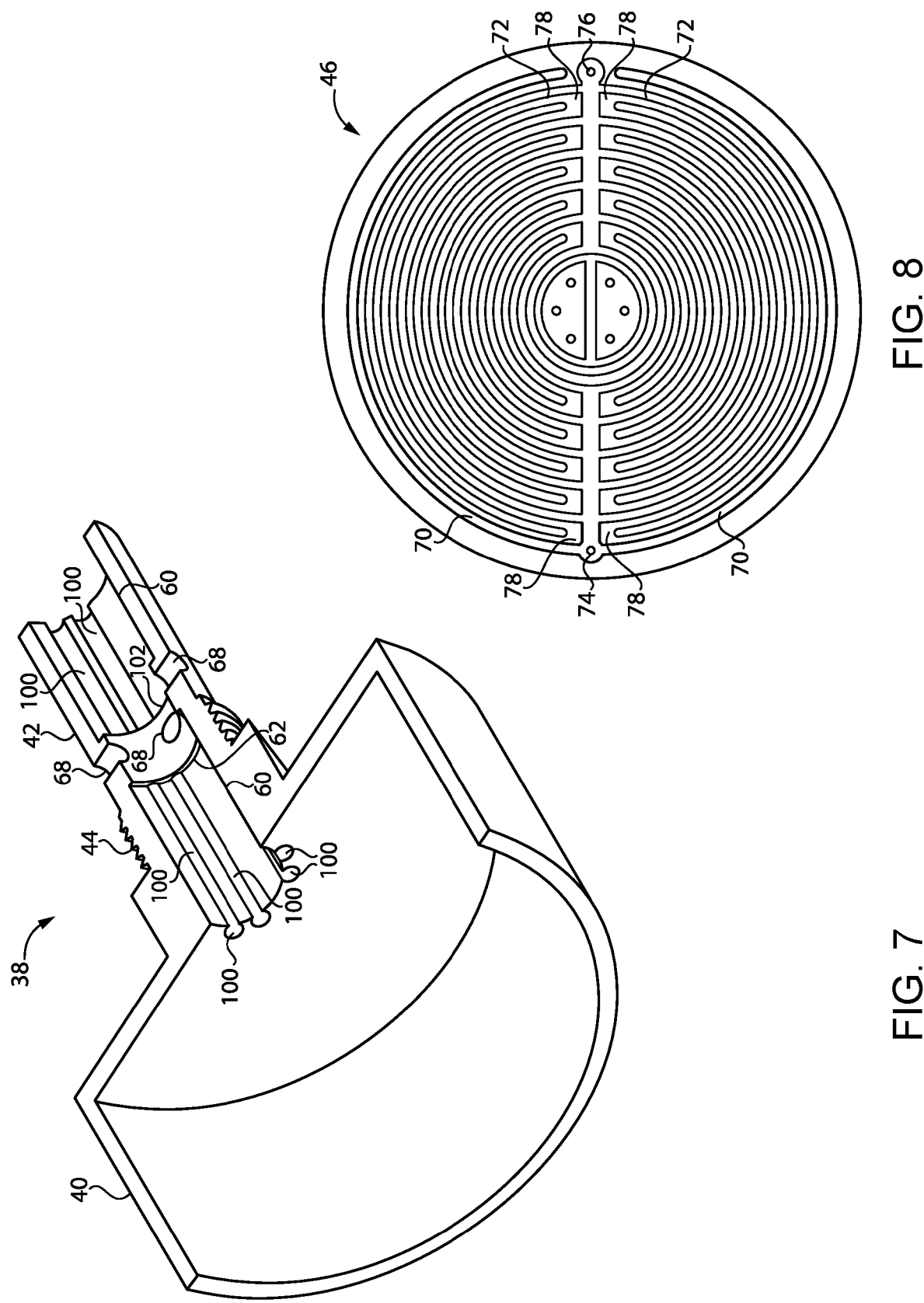

OIL QUALITY SENSOR

BACKGROUND

The present inventions relate generally to oil monitoring, and more particularly, to a sensor for monitoring oil quality in machinery like gearboxes, transmissions, engines, etc.

One example of machinery that requires the use of oil within the machinery is known as a gearbox. Gearboxes are mechanical power transmission devices which provide speed and torque conversion from a rotating power source (driving end) to the rotating load (driven end). Speed and torque conversion is achieved through the meshing of gears with different numbers of teeth. Thus, a gear ratio may be expressed as the ratio of the number of teeth in the driven gear with the number of teeth in the driving gear.

Lubrication oil is used in the gearbox reduce surface-wear of the gear teeth and prevent corrosion and provide cooling within the interior of the gearbox. In addition to protecting the mechanical components in the gearbox, lubrication oil can also be used a strong indicator of the operating and health condition of the gearbox. Thus, continual monitoring of oil quality is particularly useful. When continual oil quality monitoring is implemented, it is expected that gearbox maintenance costs would be reduced and the equipment lifecycle would be increased. However, gearbox oil is typically analyzed offline with samples of oil being periodically extracted from the gearbox and examined in dedicated laboratories. While providing advantages of continual monitoring, offline analysis is costly in terms of time, human resources and the overall equipment utilization rate.

In an attempt to minimize the costs related to gearbox oil analysis, online monitoring of the oil is possible while the oil remains in the gearbox using one or more sensors connected to the gearbox. Online oil quality monitoring may be used for various lubrication designs. For example, in one type of design known as an oil bath, gears are immersed in a reservoir filled with the lubricant oil. In another design, forced lubrication is used where oil is pumped in and out of the reservoir. In the first example, an oil sensor may be mounted in the gear housing, and in the second example, a sensor may be mounted along the lubrication path without direct contact with the gear housing.

Possible oil properties that may be monitored to determine oil quality include electrical properties, thermal properties and optical properties. Online monitoring of oil quality can be reliable in some situations but still has a relatively low accuracy in determining actual oil quality. Low-accuracy sensors lead to additional maintenance costs if the sensor indicates an oil change is needed sooner than is actually needed. This can cause unnecessarily frequent oil changes. On the other hand, oil sensors may also indicate that an oil change is required later than when actually needed. In this scenario, the health of the gearbox will deteriorate as the lubricant loses its properties.

Current oil sensors are also typically wired sensors which in some cases require an additional unit containing the electronic circuitry. Such solutions are far from practical with regards to installation in harsh industrial environments where gearboxes operate. Additionally, current oil sensors can be expensive, and thus, are not used in many applications.

Accordingly, the inventors believe an improved oil quality sensor would be desirable.

SUMMARY

A sensor is described for monitoring the quality of oil in various types of mechanical machinery, such as gearboxes, transmissions, engines, etc. The sensor includes a sealed portion and a portion that is exposed to the oil. The sealed portion contains electrical circuitry for processing sensor data collected by the sensor. The portion that is exposed to the oil contains one or more sensing elements for sensing one or more properties of the oil. Oil properties that may be sensed by the sensor include electrical properties, temperature properties and/or optical properties. The invention may also include any other aspect described below in the written description or in the attached drawings and any combinations thereof.

BRIEF DESCRIPTION OF SEVERAL VIEWS OF THE DRAWINGS

The invention may be more fully understood by reading the following description in conjunction with the drawings, in which:

FIG. 7 is a perspective cross-sectional view of a housing for the sensor;
FIG. 8 is a front view of a capacitor board for the sensor.

DETAILED DESCRIPTION

The oil quality sensor provides an assessment of oil quality by monitoring one or more of three possible properties of oil including electrical, thermal and optical properties. In the ideal sensor, a single device may be used to monitor all three properties of oil. The sensor's probe may be immersed in an oil reservoir of a gearbox or may be located in an oil passageway. An electric circuit in a sealed portion of the sensor may collect data from the sensor(s) of the device and electronically process the data to determine the oil quality. As a result, accurate online monitoring of oil quality is possible. It is also desirable for the oil quality sensor to be wireless. That is, power may be provided by an onboard battery without the need for power connections, and sensor outputs may be wirelessly communicated, e.g., with Bluetooth Low Energy (BLE) technology.

Benefits of the oil quality sensor include the ability to evaluate the current health of a gearbox using oil quality and identify gear boxes that are exhibiting signs of degradation or that are operating under higher stress. Gearbox maintenance costs may also be reduced and equipment lifecycle may be increased. The costs of gearbox lubrication oil analysis may also be reduced by avoiding periodic oil sample analysis. Wireless communication with the sensor may also simplify use of the oil sensor. Further, safety for maintenance personnel may be improved since personnel do not need to climb on structures to locate a gearbox and take physical samples of the oil.

Figure 1:
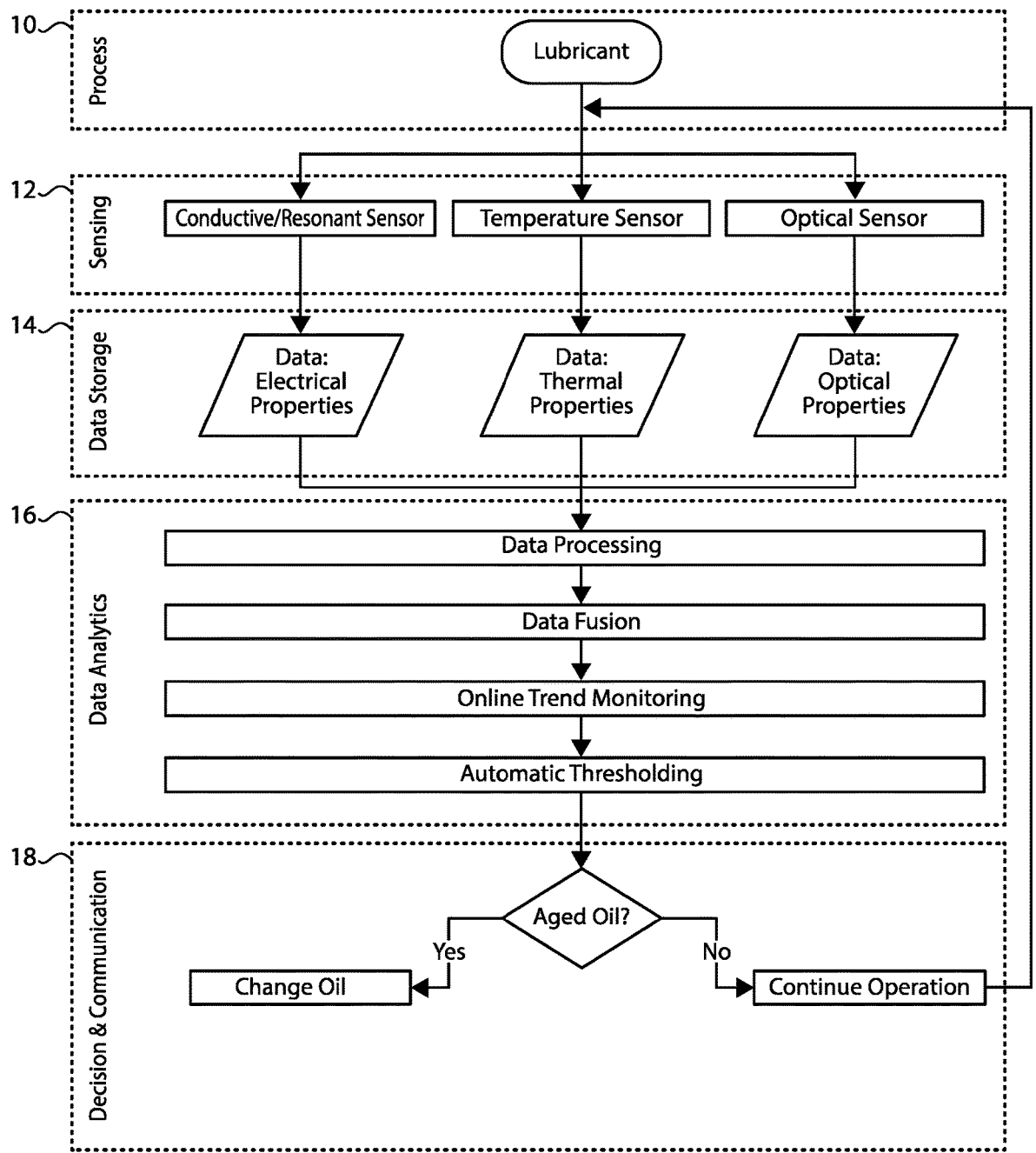
FIG. 1 is a flow chart of a sensor monitoring system.

The sensor may monitor the electrical, thermal and/or optical properties of oil via three possible sensors. In FIG. 1, a flow diagram shows a sequence of actions followed by the sensor in order to determine oil quality. The lubricant oil is located inside and circulates in a gearbox or other mechanical machinery 10. Electrical properties may be monitored through a conductive/resonant sensor 12. Temperature changes may be measured with a temperature sensor 12. And an optical sensor may indicate changes of lubricant oil's optical properties 12. Physical variables are transduced to raw signals by the aforementioned sensors. Raw signals may then be stored for a comprehensive analysis in the succeeding stage 14. In the data analytics stage, data processing, data fusion, online trend monitoring and automatic thresholding may be performed 16. This stage generates information needed for the decision layer to decide whether it is time to change the oil or not 18. After a decision has been made, the sensor may communicate the decision and/or collected data to the user via BLE.

Figure 2:
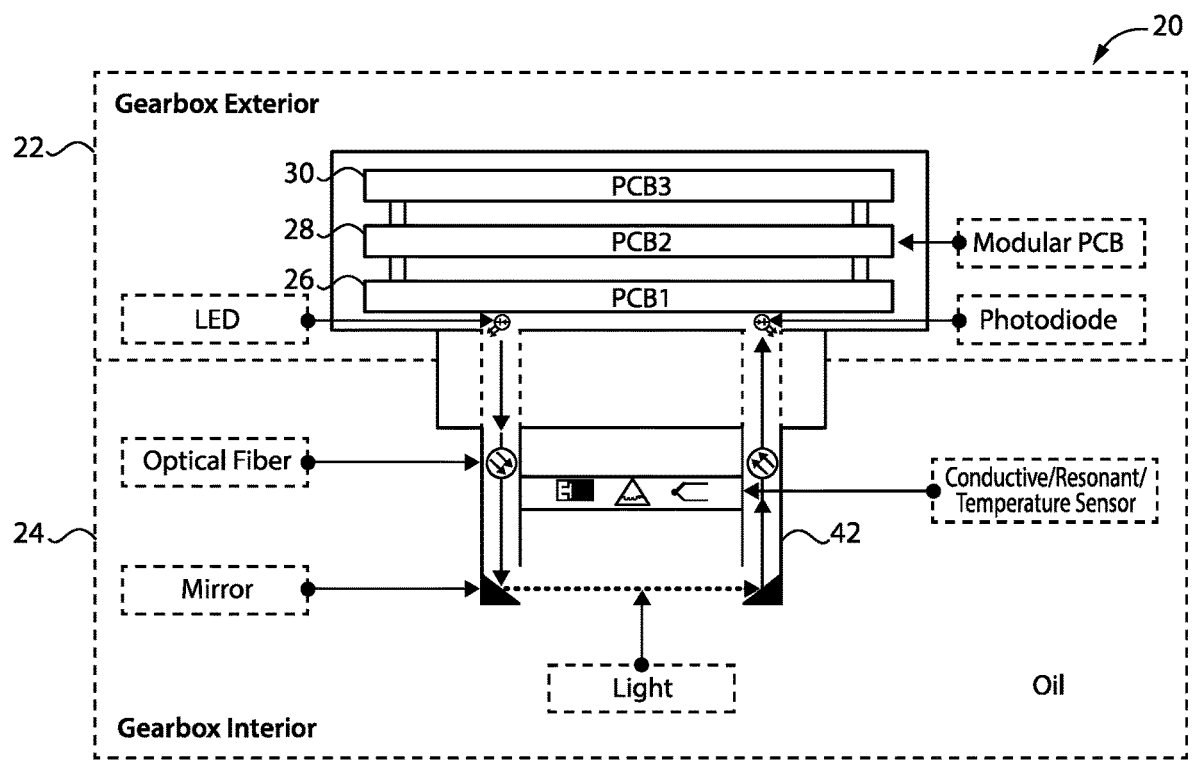
FIG. 2 is a schematic of a sensor.
Figure 3:
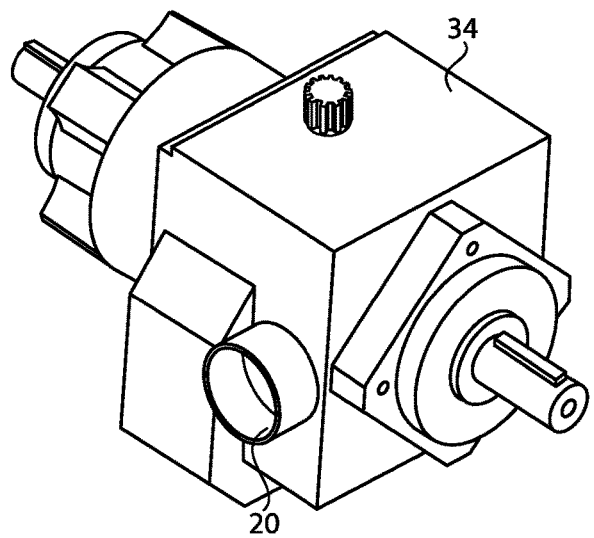
FIG. 3 is a perspective view of a gearbox.

FIG. 2 illustrates a functional schematic of the sensor 20. The sensor may be divided into two portions: the gearbox exterior which is sealed from the oil 22, and gearbox interior which is exposed to the oil 24. Electronic circuitry of the sensor may include one or more Printed Circuit Boards (PCB) 26, 28, 30 located in the sealed gearbox exterior area 22. The sensing probe 42 of the sensor 20 is preferably in direct contact with the oil in the interior part of the gearbox 34. The sealed portion 22 may be sealed from the oil exposed portion 24 with adhesive or other sealing material between the optical fibers 50 and the optical fiber recesses 100 and between the capacitor board 46 and the tubular portion 60 and step 62 of the probe portion 42 (see FIG. 7). Any other conventional sealing techniques may also be used which are capable of withstanding the high oil temperatures (e.g., up to 125° C.) that the sensing probe 42 will be exposed to. The sensing components of the sensor 20 will be described in further detail below. The sensor 20 may be mounted at different locations on the gearbox 34 as desired. For example, a radial positioning of the sensor 20 with respect to a gearbox 34 is shown in FIG. 3.

Figure 4:
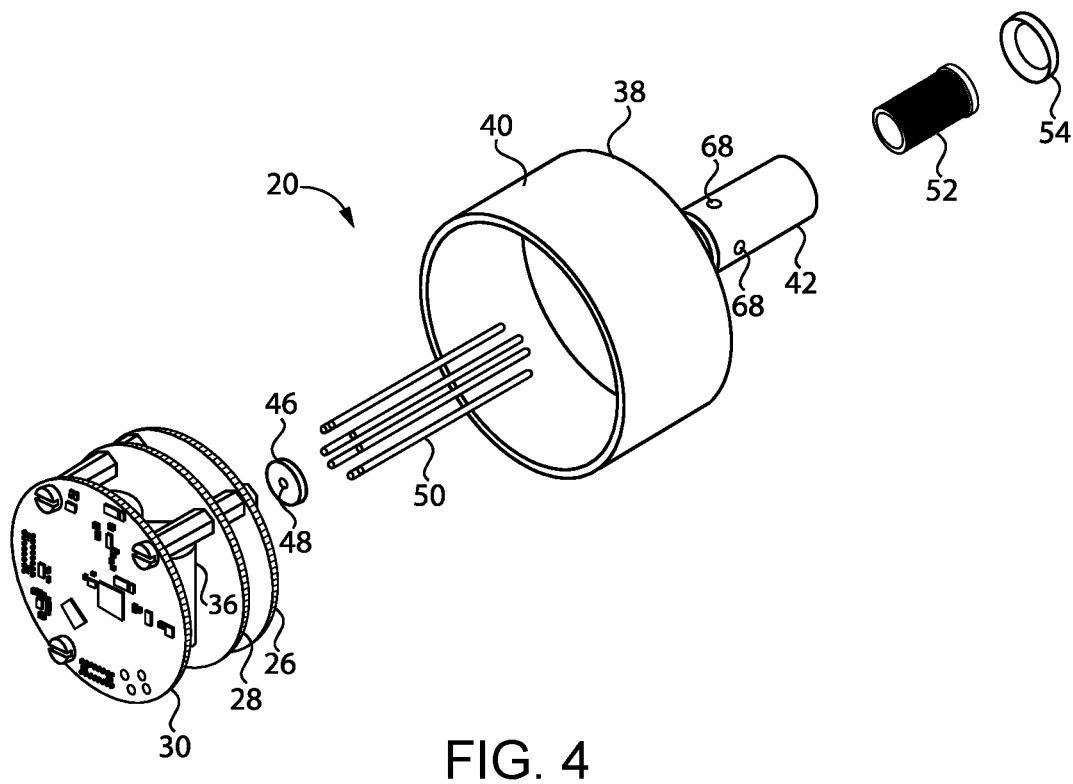
FIG. 4 is an exploded view of the sensor.

FIG. 4 illustrates an exploded view of the sensor 20. The modular PCB may include three PCBs, with a main board 30, an impedance spectroscopy board 28 and an optical board 26. A battery 36 may also be provided on one of the boards to provide power for the sensor 20. The main board 30 preferably performs the following: action control, data processing, data storage, communication via BLE and power supply. The impedance spectroscopy board 28 preferably performs necessary signal conditioning for the resonant sensor and a connection to temperature sensor. The optical board 26 is preferably responsible for sequential LED switching, LED current control and photodiode response conversion (current-to-voltage and analog-to-digital). The electric circuitry of the modular PCB 26, 28, 30 may be located in a sealed circuit board enclosure portion 40 of the sensor housing 38.

Figure 5:
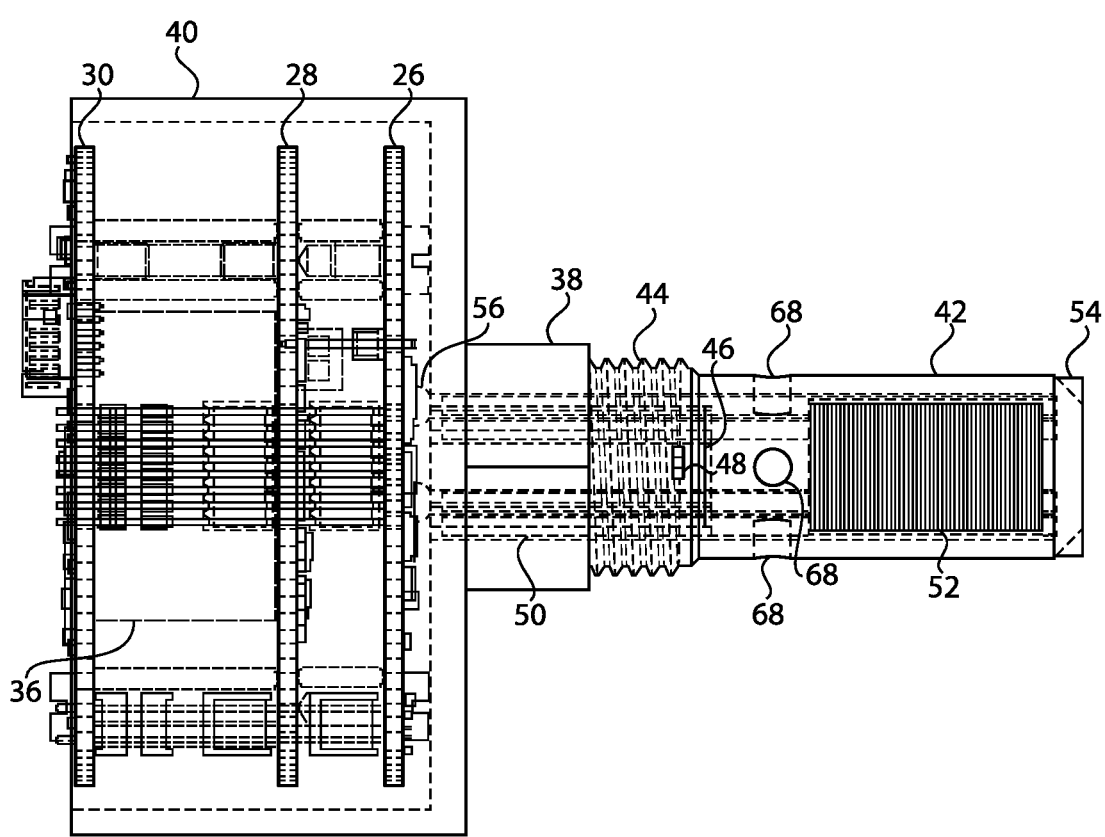
FIG. 5 is a side cross-sectional view of the sensor.
Figure 6:
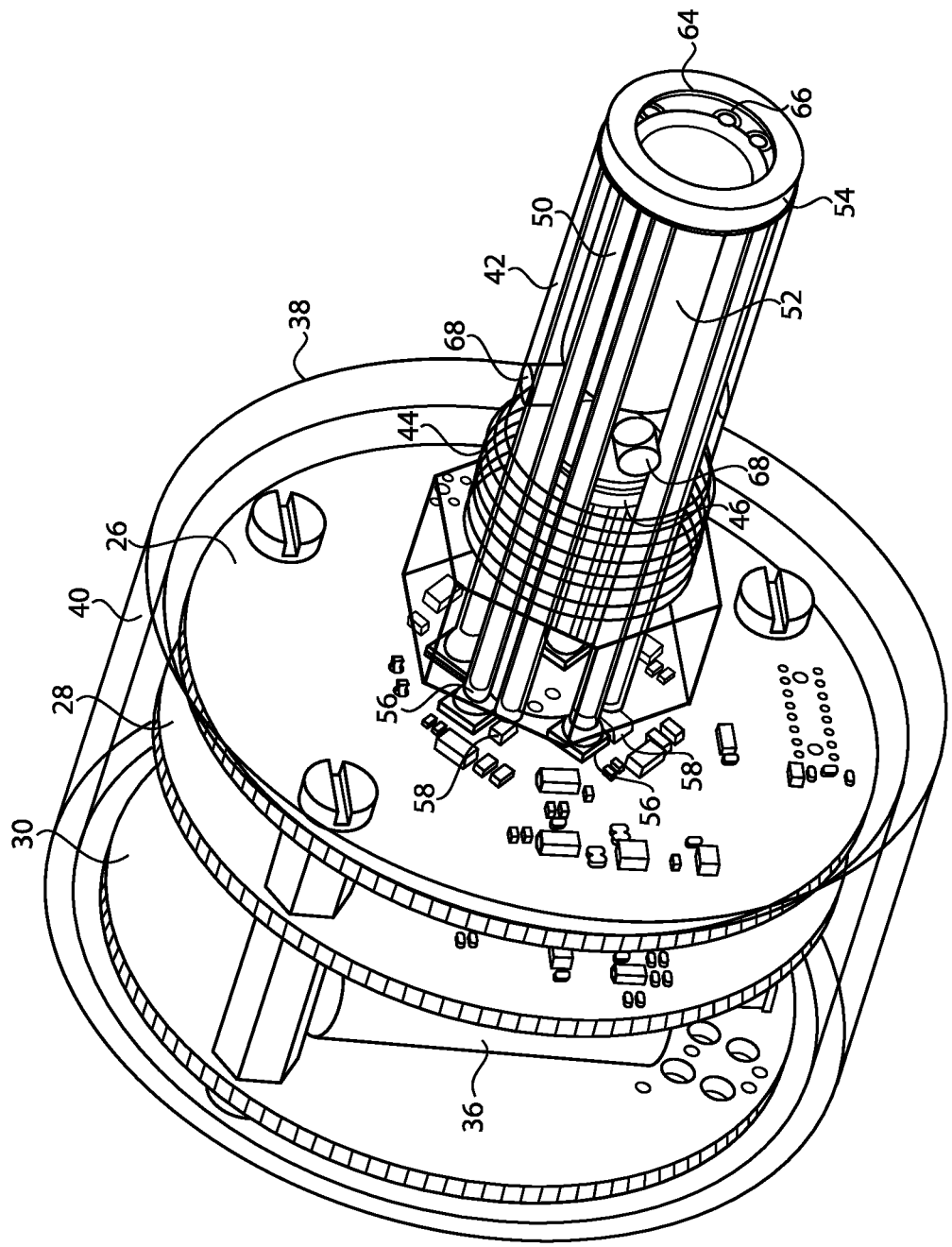
FIG. 6 is a perspective view of the sensor.

The housing 38 may also include a probe portion 42 which is in direct contact with the oil. Preferably, the probe portion 42 is cylindrical in order to be inserted through a threaded hole in the gearbox 34. The cylindrical probe portion 42 may also include threads 44 (FIG. 5) in order to thread the probe portion 42 into the threaded hole in the gearbox 34. The probe portion 42 may include a coplanar capacitor 46, a temperature sensor 48, optical fibers 50, an inductor 52 and an optical mirror 54, which will each be described further below. FIG. 5 is a side view that further shows an arrangement of the components in the circuit board enclosure 40 and the probe portion 42. A position of the LEDs 56 and the photodiodes 58 on the optical board 26 is also shown in FIGS. 5 and 6.

One possible sensing system that may be incorporated into the sensor 20 is a conductive and/or resonant electrical property sensor. The conductive/resonant sensor may be an electrical circuit including two passive components, i.e., a coplanar capacitor 46 and an inductor 52. The electrical property sensor may be used to sense impedance changes at frequencies of interest (e.g., resonant frequencies) of the circuit when immersed in the lubricating oil. During operation of a gearbox, lubricant oil is subjected to phenomena such as increased temperature, elevated concentration of ferrous particles, oxidation and sometimes increased water concentration. The majority of these changes are caused by the repeated meshing of the gear teeth. Changes in the oil's dielectric permittivity, magnetic permeability or conductivity may be used as an indicator of these changed conditions of the oil. One indicator measured by the electrical property sensor is the impedance of the circuit at different frequencies, including the resonant frequency. Changes in the impedance may indicate degradation of the oil.

FIG. 8 shows one embodiment of the coplanar capacitor 46. In use, the face of the coplanar capacitor 46 is preferably exposed to the oil. That is, the coplanar capacitor 46 may be assembled into a tubular portion 60 of the probe portion 42 from the circuit board enclosure 40 and bottomed against a step 62. During use, oil may flow through the open middle 64 of the mirror 54, through the open center 66 of the inductor 52, and through radial openings 68 through the side of the probe portion 42. The coplanar capacity may have interleaved arc-shaped conductors 70, 72 coupled to opposite terminals 74, 76, respectively. The conductors 70, 72 and terminals 74, 76 may be embedded in a dielectric pre-preg material 78 commonly used for PCBs. Soldering pads 80, 82 may be provided on the backside of the coplanar capacitor board 46 for soldering electrical connections to the impedance board 28 and leads to the inductor 52. The soldering pads 80, 82 may be electrically connected to the capacitor 46 terminals 74, 76 with vias through the thickness of the board 46.

Depending on the exposure of the conductors (electrodes) 70, 72, the electrical property sensor may perform different functions. For example, when electrodes 70, 72 are not exposed (e.g., a solder mask is used to electrically insulate them from physical contact with the oil), only dielectric permittivity may be monitored through the capacitance value between two terminals 74, 76. On the other hand, if the electrodes 70, 72 are exposed (i.e., directly contacting the oil without an electrically insulating covering layer), in addition to permittivity, conductivity of the oil may be monitored as well. Thus, the electrical property sensor is referred to herein as a conductive/resonant sensor in that the actual functionality of the sensor can vary depending on the desired use.

Figure 9:
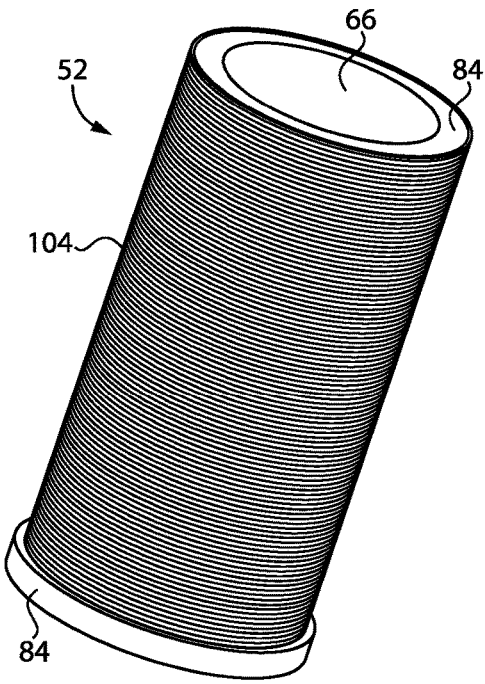
FIG. 9 is a perspective view of an inductor for the sensor.
Figure 10:
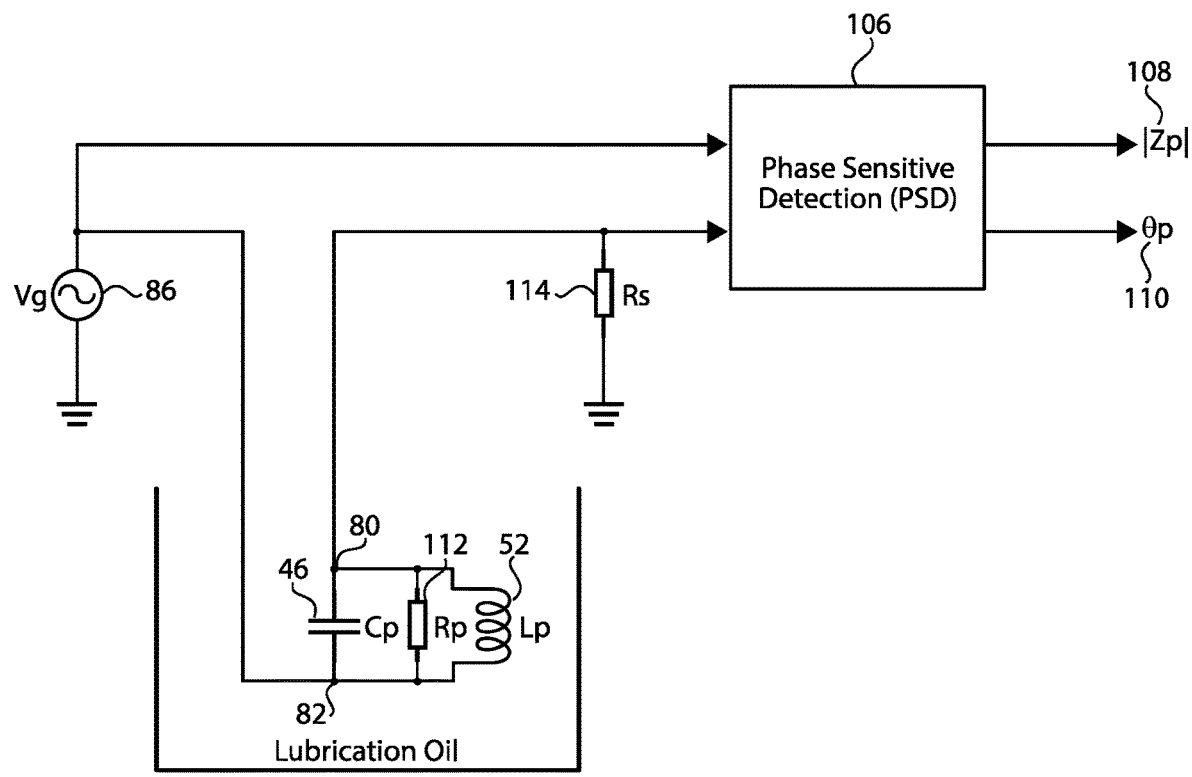
FIG. 10 is an electrical schematic of an electrical property sensing system for the sensor.

In FIG. 9, the inductor 52 of the resonant sensor is shown. The inductor 52 may be an air core helically wound coil 104 wrapped around an electrically insulative plastic cylindrical tubular structure 84 made of a plastic material with high mechanical resistance, chemically inert and high temperature resistance (e.g., PolyEtherEtherKeton—PEEK). The inner surface of the plastic core 84 material is intended to be in direct contact with the lubricant oil to allow oil to flow through the open center 66 of the inductor 52. Thus, the core 84 is preferably resistant to harsh conditions of oil in the interior of the gearbox. The capacitor 46 and the inductor 52 may be electrically connected in parallel to each other as illustrated in the schematic in FIG. 10, although other arrangements may also be possible such as an in series connection. An AC frequency generator 86 may be provided on the impedance board 28 to supply a varying frequency signal to the capacitor 46 and inductor 52 in order to sense electrical properties of the oil. Sensing of the electrical properties may be done with a phase sensitive detection circuit 106, which may also be located on the impedance board 28. Thus, the outputs may be a probe impedance modulus (|Zp|) 108 and a probe impedance phase angle (θp) 110. An equivalent probe parallel resistance 112 may also be desirable in parallel with the capacitor 46 and the inductor 52, and a sense resistor 114 may also be desirable between the capacitor terminal 80 and ground. By immersing the conductive/resonant circuit in the oil reservoir of a gearbox, the electrical property sensor may be able to monitor dielectric permittivity, conductivity and magnetic permeability of the oil at specific frequencies of the impedance spectrum. As shown in FIG. 7, the inductor 52 may be assembled into the tubular portion 60 of the probe portion 42 through the end of the probe portion 42 until the inductor 52 abuts a step 102 therein.

Figure 11:
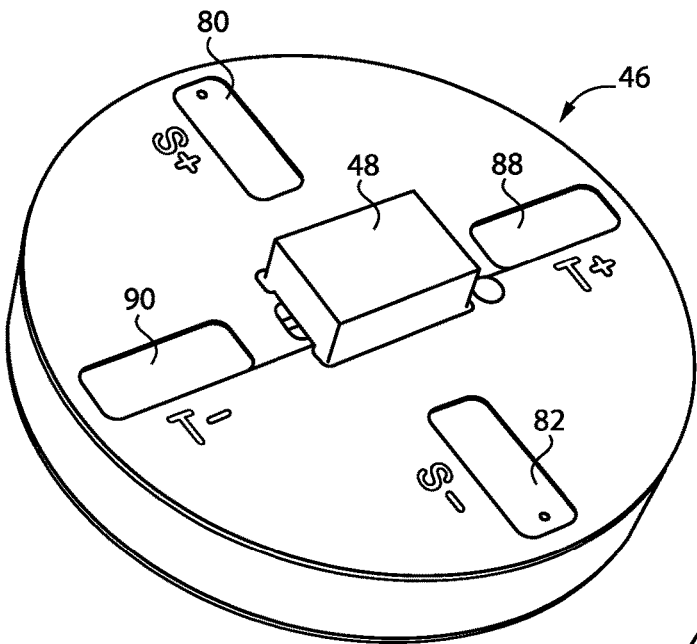
FIG. 11 is a perspective rear view of the capacitor board.
Figure 11A:
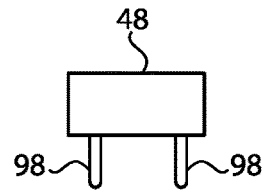
FIG. 11A is a side view of a temperature sensor for the sensor.
Figure 12:
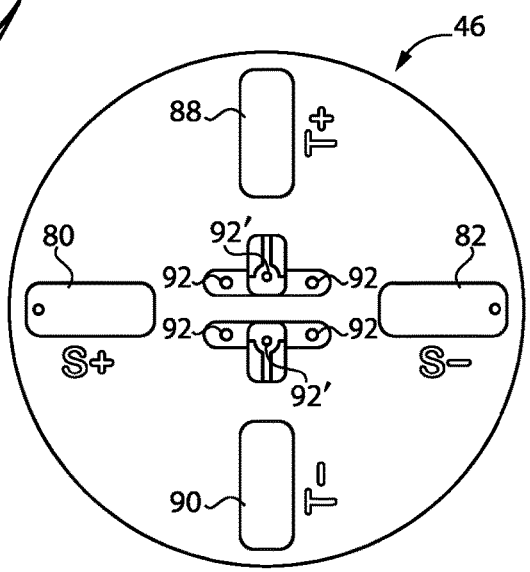
FIG. 12 is a rear view of the capacitor board with the temperature sensor removed.
Figure 13:
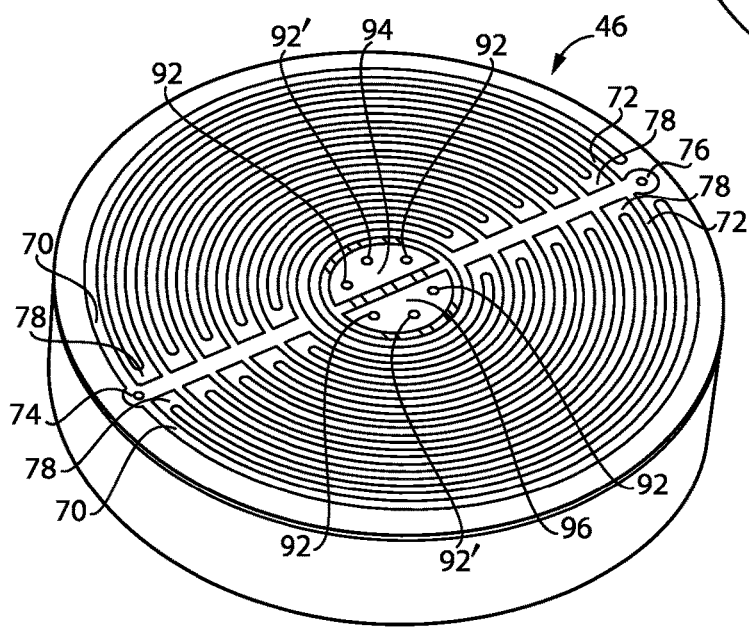
FIG. 13 is a perspective front view of the capacitor board.

Another possible sensing system that may be incorporated into the sensor 20 is a temperature sensor 48. As shown in FIG. 11, the temperature sensor 48 may be attached to the backside of coplanar capacitor board 46. Preferably, the temperature sensor 48 is positioned in the center of coplanar capacitor board 46. Soldering pads 88, 90 may be electrically connected with conductive lines to the power supply terminals of the sensor 48 which may also provide transmission of the measured signal. The soldering pads 88, 90 may be electrically connected to the main board 30. The temperature sensor 48 preferably does not have physical contact with the lubricant in order to preserve the life of the sensor 48. The location of the temperature sensor 48 on the backside of the capacitor board 46 also makes it more convenient to incorporate both sensors in the same sensor module 20 and housing 38. The sensor 48 may be thermally connected with the oil via thermal vias 92 through the thickness of the capacitor board 46, which acts as a insulative plate between the sealed portion 22 of the sensor 20 and the oil exposed portion 24 of the sensor 20. FIGS. 12-13 indicate positions that may be provided for six thermal vias 92 in the center of the board 46 connected to a pair of thermal plates 94, 96 (i.e., thermally conductive surfaces) which increase the contact surface with oil. The thermal plates 94, 96 may be located on the same side of the capacitor board 46 in the center of the arc-shaped conductors 70, 72. As described, the oil is allowed to contact the thermal plates 94, 96 through the open middle 64 of the mirror 54 and the open tubular center 66 of the inductor 52. In order to allow the electrodes 98 (FIG. 11A) of the temperature sensor 48 to be soldered to the board 46 through the two middle vias 92', the thermal plates 94, 96 are preferably electrically separated from each other. Thus, the vias 92 and thermal plates 94, 96 function both as thermally conductive structures to transfer heat from the oil to the temperature sensor 48 and also as electrical connections for the electrodes 98 of the temperature sensor 48.

Figure 14:
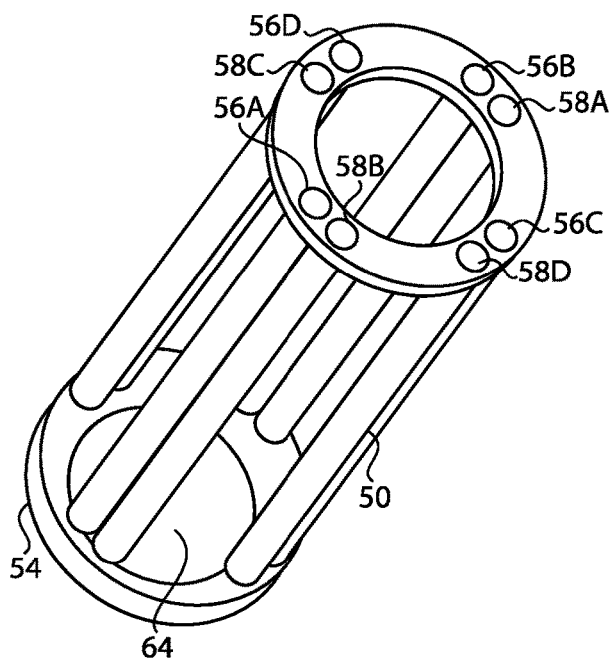
FIG. 14 is a perspective view of optical fibers and a mirror for the sensor.
Figure 15:
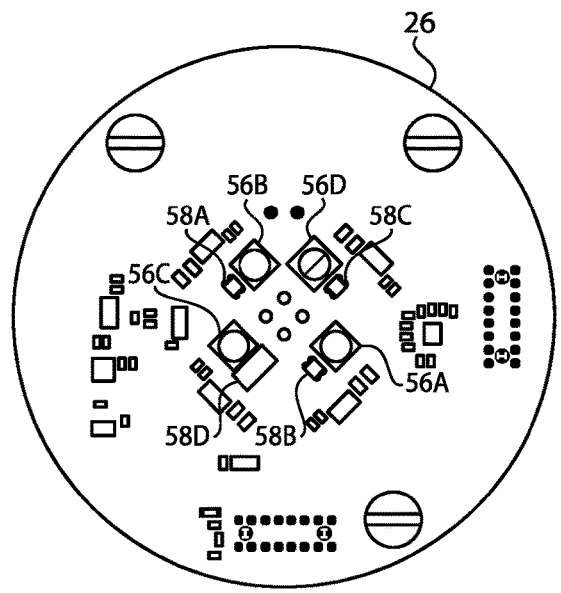
FIG. 15 is a front view of an optical board for the sensor.
Figure 16:
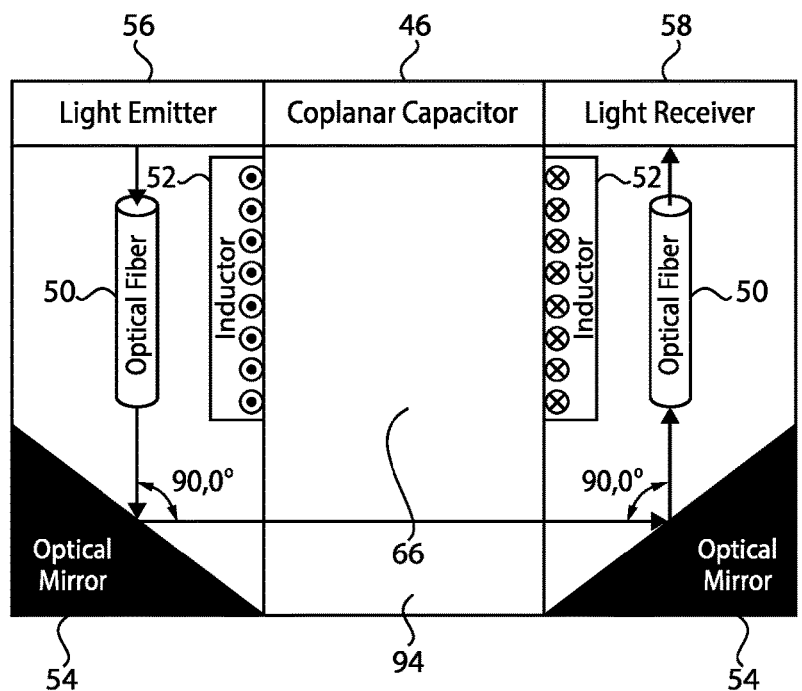
FIG. 16 is a schematic of a probe portion of the sensor.

Another possible sensing system that may be incorporated into the sensor 20 is an optical property sensor. The optical property sensor may use light to indicate the age of the oil. As shown in FIG. 16, light may travel across the transmission medium which in this case is lubrication oil in a gearbox. Response attenuation may be measured on the other end of the transmission medium. The optical sensing system may be oriented along the axis of probe portion 42. Preferably, the system includes eight optical fibers 50, an optical mirror 54, a blue LED 56A, a red photodiode 58B, an infrared photodiode 58D, a green LED 56C, a blue photodiode 58A, a red LED 56B, an infrared LED 56D, and a green photodiode 58C. FIG. 15 shows locations for the LEDs 56 and photodiodes 58 on the optical board 26, and FIG. 14 provides corresponding labels indicating how the optical fibers 50 are lined up with the LEDs 56 and photodiodes 58 when the sensor 20 is assembled. The optical sensor may use four LEDs to emit light at different wavelengths, e.g., $\lambda_R$(625 nm), $\lambda_G$(528 nm), $\lambda_B$(458 nm) and $\lambda_{IR}$(950 nm). A number of wavelengths may be used in order to monitor different indicators (e.g., the presence of different sizes of ferrous and nonferrous particles).

Preferably, the LEDs 56 and photodiodes 58 are arranged in a circular layout around the center of the optical board 26 within the sealed portion 22 of the sensor 20. The optical fibers 50 are also arranged in a corresponding circular arrangement and may extend longitudinally around the outside of the inductor 52 such that the inductor 52 is positioned within and between the optical fibers 50. Light is guided by the optical fibers 50 from the LEDs 56 to the optical mirror 54 and back from the mirror 54 to the photodiodes 58. The mirror 54 may be a ring-shaped mirror 54 which deflects light 90° from the LED optical fibers 50 to the other side of the mirror 54 and deflects the light again 90° to the photodiode optic fibers 50. In passing from one side of the mirror 54 to the other side of the mirror 54, the light preferably passes across the center of the ring-shaped mirror 54. Further, between the two sides of the mirror 54, the light passes through the oil since the open middle 64 of the mirror 54 permits oil to flow therethrough. In order to prevent obstruction between the ends of the optical fibers 50 and the mirror 54, the mirror 54 may be secured to the end of the probe portion 42 along the outer edge of the mirror 54 and the outer surface of the probe portion 42. By arranging the optical fibers 50 in a circular arrangement, the optical sensor may be designed more compactly within the circular probe portion 42. However, this design results in each of the LEDs 56 emitting light across a common center of the probe portion 42. Therefore, it is preferable that each of the LEDs 56 be operated at different times to prevent the light from two LEDs 56 crossing each other at the same time. As shown in FIG. 7, circular recesses 100 may be provided through the wall of the probe portion 42 for the optical fibers 50 to extend longitudinally therealong. As shown in FIGS. 7 and 14, it may also be desirable to space apart adjacent optical fibers 50 to allow space for the radial holes 68 to extend through the probe portion 42 between adjacent optical fibers 50. As noted above, the radial holes 68 allow oil to flow into and out of the probe portion 42, in addition to oil flowing through the tubular portion 60 and into and out of the probe portion 42 through the open middle 64 of the mirror 54.

While preferred embodiments of the inventions have been described, it should be understood that the inventions are not so limited, and modifications may be made without departing from the inventions herein. While each embodiment described herein may refer only to certain features and may not specifically refer to every feature described with respect to other embodiments, it should be recognized that the features described herein are interchangeable unless described otherwise, even where no reference is made to a specific feature. It should also be understood that the advantages described above are not necessarily the only advantages of the inventions, and it is not necessarily expected that all of the described advantages will be achieved with every embodiment of the inventions. The scope of the inventions is defined by the appended claims, and all devices and methods that come within the meaning of the claims, either literally or by equivalence, are intended to be embraced therein.

What is claimed is:

1. An oil quality sensor, comprising:
a first portion configured to be exposed to oil;
a second portion configured to be sealed from the oil;
an inductor disposed within the first portion;
a coplanar capacitor disposed within the first portion and electrically coupled with the inductor; and
a phase sensitive detector disposed within the second portion and configured to output a probe impedance modulus and a probe impedance phase angle of a circuit comprising the inductor and the coplanar capacitor;
a first optical fiber configured to emit light into the oil;
a second optical fiber configured to receive light from the oil; and
a mirror disposed between the first and second optical fibers and configured to direct the light from the first optical fiber to the second optical fiber,
wherein the probe impedance modulus and the probe impedance phase angle are used to determine quality of the oil, and
wherein the mirror comprises an open middle.

2. The oil quality sensor according to claim 1, wherein the inductor is a coil helically wound around an electrically insulative tube, the oil being disposed inside of the electrically insulative tube.

3. The oil quality sensor according to claim 1, wherein coplanar conductors of the coplanar capacitor are electrically insulated from the oil.

4. The oil quality sensor according to claim 1, wherein the circuit comprises an AC frequency generator coupled to the inductor and configured to generate a varying frequency signal in the inductor.

5. The oil quality sensor according to claim 1, further comprising a thermally conductive surface configured to transfer heat to a temperature sensor.

6. The oil quality sensor according to claim 5, wherein the temperature sensor is disposed in the second portion.

7. The oil quality sensor according to claim 6, further comprising an insulative plate between the first portion and the second portion, and a heat transfer via extending through the insulative plate, the heat transfer via being coupled to the thermally conductive surface and the temperature sensor.

8. The oil quality sensor according to claim 5, wherein a first electrode of the temperature sensor is coupled to the thermally conductive surface and a second electrode of the temperature sensor is coupled to another thermally conductive surface.

9. The oil quality sensor according to claim 1, further comprising a third optical fiber configured to emit light into the oil and a fourth optical fiber configured to receive light from the oil, wherein the mirror is disposed between the first and second optical fibers and between the third and fourth optical fibers such that paths of the light emitted from the first optical fiber and the third optical fiber cross each other, and wherein the light emitted from the first optical fiber and the light emitted from the third optical fiber are emitted at different times.

10. The oil quality sensor according to claim 1, further comprising an LED and a photodiode disposed within the second portion, wherein the LED is configured to emit light into the first optical fiber, and the photodiode is configured to receive light from the second optical fiber.

11. The oil quality sensor according to claim 1, further comprising a third optical fiber configured to emit light into the oil, the second optical fiber being adjacent one side of the first optical fiber and the third optical fiber being adjacent another side of the first optical fiber, a space between the first and second optical fibers being greater than a space between the first and third optical fibers, the first portion comprising a cylindrical probe portion, the first, second and third optical fibers extending longitudinally along the cylindrical probe portion, and a radial opening through the cylindrical probe portion extending between the first and second optical fibers to allow oil to flow into or out of the cylindrical probe portion.

12. The oil quality sensor according to claim 1, further comprising a thermally conductive surface configured to transfer heat to a temperature sensor, wherein the coplanar capacitor and the thermally conductive surface are both disposed on a same side of an insulative plate.

13. The oil quality sensor according to claim 1, further comprising a thermally conductive surface configured to transfer heat to a temperature sensor, wherein the inductor is a coil helically wound around a tube, and the oil contacts the thermally conductive surface through the tube.

14. The oil quality sensor according to claim 1, wherein the inductor is a helically wound coil disposed between the first and second optical fibers.

15. The oil quality sensor according to claim 1, further comprising a housing, the first portion comprising a cylindrical probe portion of the housing, and the second portion comprising a circuit board enclosure, the inductor and the capacitor being disposed within the cylindrical probe portion, and the phase sensitive detector being disposed on a circuit board within the circuit board enclosure.

16. The oil quality sensor according to claim 1, wherein the capacitor and the inductor are electrically connected in parallel.

17. The oil quality sensor according to claim 16, further comprising an equivalent probe parallel resistance in parallel with the capacitor and the inductor, and a sense resistor between a terminal of the capacitor and ground.

18. The oil quality sensor according to claim 13, further comprising vias extending through a thickness of the capacitor, wherein the vias are configured to conduct heat from the oil to the temperature sensor and to conduct electricity to electrodes of the temperature sensor.

19. The oil quality sensor according to claim 1, wherein the probe impedance modulus and the probe impedance phase angle are further used to determine whether to change the oil.

20. The oil quality sensor of claim 15, wherein the mirror is secured to an end of the cylindrical probe portion along an outer edge of the mirror and an outer surface of the cylindrical probe portion.

21. An oil quality sensor, comprising:
a first portion exposed to the oil;
a second portion sealed from the oil;
an inductor disposed within the first portion and configured to sense a property of the oil;
an electric circuit disposed within the second portion and configured to electronically process the property of the oil;
thermal plates configured to transfer heat to a temperature sensor;
a first optical fiber configured to emit light into the oil;

a second optical fiber configured to receive light from the oil; and a mirror disposed between the first and second optical fibers and configured to direct the light from the first optical fiber to the second optical fiber, wherein the mirror comprises an open middle.

22. The oil quality sensor according to claim 21, further comprising a coplanar capacitor.

23. The oil quality sensor according to claim 22, wherein conductors of the coplanar capacitor are configured to contact the oil.

24. The oil quality sensor according to claim 22, wherein the electric circuit comprises an AC frequency generator coupled to the coplanar capacitor and configured to generate a varying frequency signal in the coplanar capacitor.

25. The oil quality sensor according to claim 21, wherein the thermally conductive surface is electrically conductive.

26. The oil quality sensor of claim 21, wherein the mirror and the inductor are configured such that the oil contacts the thermal plates through the open middle and an open tubular center of the inductor.

27. An oil quality sensor, comprising:
a first portion exposed to the oil;
a second portion sealed from the oil;
a first sensing element disposed within the first portion and configured to sense a property of the oil;
an electric circuit disposed within the second portion and configured to electronically process the property of the oil,
wherein the first sensing element comprises an inductor, and a coplanar capacitor electrically coupled with the inductor, and wherein coplanar conductors of the coplanar capacitor are electrically insulated from the oil;
a second sensing element comprising a first optical fiber configured to emit light into the oil;
a second optical fiber configured to receive the emitted light from the first optical fiber from the oil;
a mirror between the first and second optical fibers and configured to direct the light from the first optical fiber to the second optical fiber;
a third optical fiber configured to emit light into the oil;
a fourth optical fiber configured to receive the light emitted from the third optical fiber from the oil,
wherein the mirror is disposed between the third and fourth optical fibers such that paths of the light emitted from the first optical fiber and the third optical fiber cross each other, and the light emitted from the first optical fiber and the light emitted from the third optical fiber are emitted at different times; and
an LED and a photodiode disposed within the second portion, the LED configured to emit the light into the first optical fiber, and the photodiode configured to receive the light from the second optical fiber,
wherein the second optical fiber is adjacent one side of the first optical fiber and the third optical fiber is adjacent another side of the first optical fiber, a space between the first and second optical fibers is greater than a space between the first and third optical fibers, the first portion comprises a cylindrical probe portion, the first, second and third optical fibers extend longitudinally along the cylindrical probe portion, and a radial opening through the cylindrical probe portion extends between the first and second optical fibers to allow the oil to flow into or out of the cylindrical probe portion, and
wherein the mirror comprises an open middle.

28. The oil quality sensor of claim 27, wherein the mirror, the inductor, and the cylindrical probe portion are configured such that the oil flows through the open middle, through an open center of the inductor, and through the radial opening.

* * * * *